United States Patent [19]

Stewart et al.

[11] Patent Number: 5,128,048
[45] Date of Patent: Jul. 7, 1992

[54] SYSTEMS AND METHODS FOR REMOVING UNDESIRED MATTER FROM BLOOD CELLS

[75] Inventors: Mary A. Stewart, Mundelein; Kenneth Johnson, Lindenhurst, both of Ill.

[73] Assignee: Baxter International Inc., Deerfield, Ill.

[21] Appl. No.: 704,029

[22] Filed: May 22, 1991

[51] Int. Cl.⁵ ............... B01D 37/00; B01D 24/00; B01D 21/26; A61M 1/00

[52] U.S. Cl. .................. 210/749; 210/767; 210/782; 210/787; 210/806; 210/206; 210/257.1; 210/420; 422/41; 422/44; 604/406; 604/410

[58] Field of Search ......... 210/767, 782, 787, 789, 210/805, 806, 206, 233, 257.1, 420, 749; 422/41, 44; 604/406, 408, 410

[56] References Cited

U.S. PATENT DOCUMENTS

| | | |
|---|---|---|
| 4,267,269 | 5/1981 | Grode et al. .................. 435/2 |
| 4,767,541 | 8/1988 | Wisdom .......................... 210/787 |
| 4,855,063 | 8/1989 | Carmen et al. ................. 210/787 |
| 4,915,848 | 4/1990 | Carmen et al. ................. 210/749 |
| 4,919,823 | 4/1990 | Wisdom .......................... 210/749 |
| 4,985,153 | 1/1991 | Kuroda et al. .................. 210/782 |
| 4,997,577 | 3/1991 | Stewart .......................... 210/767 |

*Primary Examiner*—W. Gary Jones
*Attorney, Agent, or Firm*—Paul C. Flattery; Bradford R. L. Price; Daniel D. Ryan

[57] ABSTRACT

Systems and methods of collecting blood cells use a first container connected to initially collect blood. A filtration system is provided that uses two flow paths, the first being a dual purpose path that is initially used to convey plasma and platelets to a pair of transfer/storage containers. A second flow path leads to a temporary transfer container through a filtration device. The dual purpose fluid path is next used to convey blood cells, now substantially free of undesired matter, from the temporary storage container to a storage container. The filtration system is then detached from the blood collection system.

32 Claims, 4 Drawing Sheets

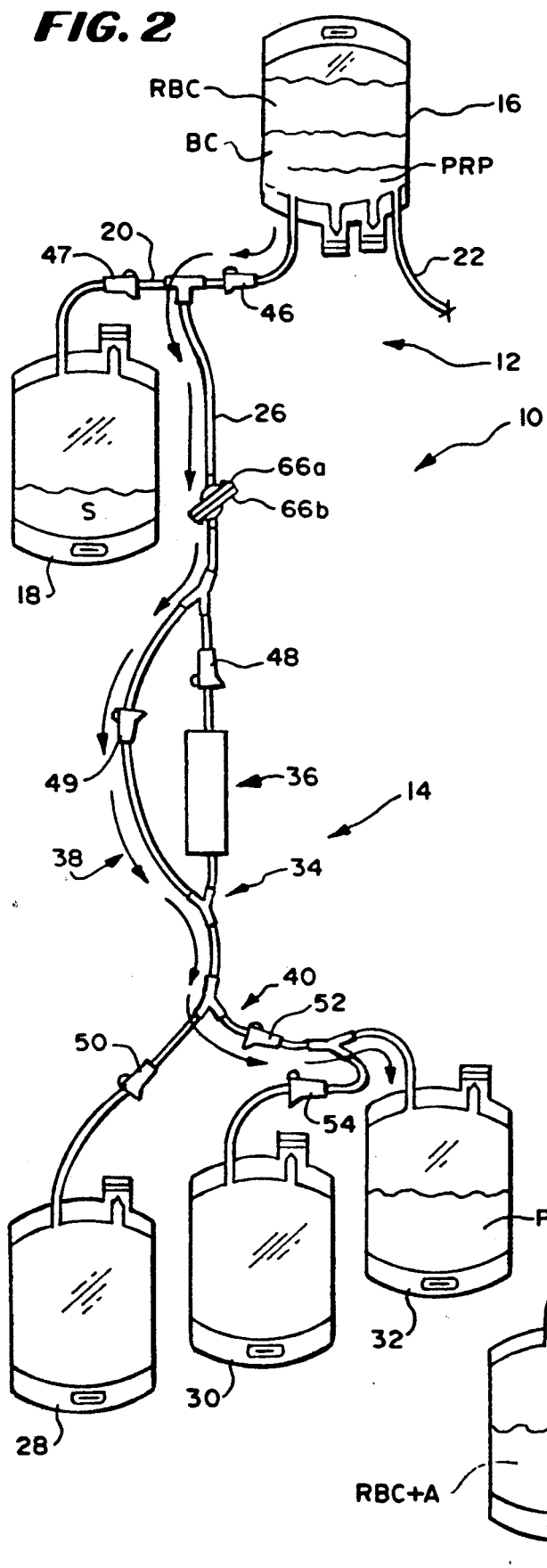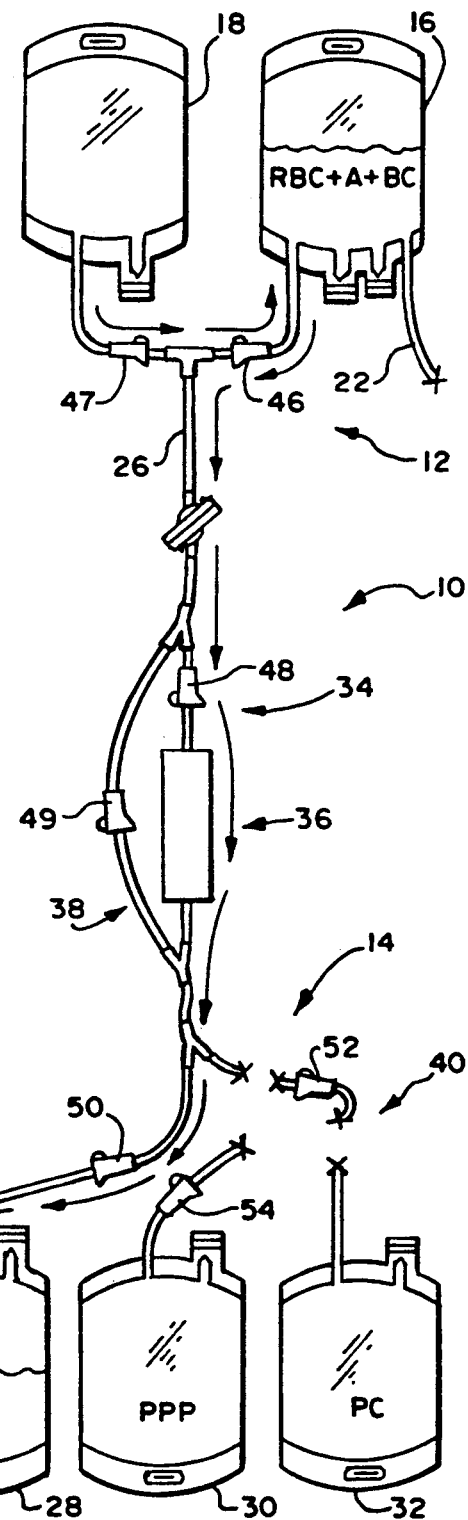
FIG. 2
FIG. 3

5,128,048

SYSTEMS AND METHODS FOR REMOVING UNDESIRED MATTER FROM BLOOD CELLS

FIELD OF THE INVENTION

The invention generally relates to blood collection and processing systems and methods. In a more particular sense, the invention relates to systems and methods for removing white blood cells from red blood cells prior to transfusion or long term storage.

BACKGROUND OF THE INVENTION

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Systems composed of multiple, interconnected plastic bags have met widespread use and acceptance in the collection, processing and storage of these blood components. In the United States, these multiple blood bag systems are subject to regulation by the government. For example, the plastic materials from which the bags and tubing are made must be approved by the government. In addition, the maximum storage periods for the blood components collected in these systems are prescribed by regulation.

In the United States, whole blood components collected in a nonsterile, or "open", system (i.e. one that is open to communication with the atmosphere) must, under governmental regulations, be transfused within twenty-four hours. However, when whole blood components are collected in a sterile, or "closed", system (i.e., one that is closed to communication with the atmosphere), the red blood cells can be stored up to forty-two days (depending upon the type of anticoagulant and storage medium used); the platelet concentrate can be stored up to five days (depending upon the type of storage container); and the platelet-poor plasma may be frozen and stored for even longer periods. Conventional systems of multiple, interconnected plastic bags have met with widespread acceptance, because these systems can reliably provide the desired sterile, "closed" environment for blood collection and processing, thereby assuring the maximum available storage periods.

In collecting whole blood components for transfusion, it is desirable to minimize the presence of impurities or other materials that may cause undesired side effects in the recipient. For example, because of possible febrile reactions, it is generally considered desirable to transfuse red blood cells substantially free of the white blood cell components, particularly for recipients who undergo frequent transfusions.

One way to remove white blood cells is by washing the red blood cells with saline. This technique is time consuming and inefficient, as it can reduce the number of red blood cells available for transfusion. The washing process also exposes the red blood cells to communication with the atmosphere, and thereby constitutes a "non-sterile" entry into the storage system. Once a non-sterile entry is made in a previously closed system, the system is considered "opened", and transfusion must occur within twenty-four hours, regardless of the manner in which the blood was collected and processed in the first place. In the United States, an entry into a blood collection system that presents the probability of non-sterility that exceeds one in a million is generally considered to constitute a "non-sterile" entry.

Another way to remove white blood cells is by filtration. Systems and methods for accomplishing this within the context of conventional multiple blood bag configurations are described in Wisdom U.S. Pat. Nos. 4,596,657 and 4,767,541, as well as in Carmen et al U.S. Pat. Nos. 4,810,378 and 4,855,063. In these arrangements, an inline white blood cell filtration device is used. The filtration can thereby be accomplished in a closed system. However, the filtration processes associated with these arrangements require the extra step of wetting the filtration device before use with a red blood cell additive solution or the like. This added step complicates the filtration process and increases the processing time.

Other systems and methods for removing white blood cells in the context of closed, multiple blood bag configurations are described in Stewart U.S. Pat. No. 4,997,577. In these filtration systems and methods, a transfer assembly dedicated solely to the removal of white blood cells is used. The transfer assembly is attached to a primary blood collection container. The transfer assembly has a transfer container and a first fluid path leading to the transfer container that includes an inline device for separating white blood cells from red blood cells. The transfer assembly also has a second fluid path that bypasses the separation device. Using these systems and methods, white blood cells are removed as the red blood cells are conveyed to the transfer container through the first fluid path. The red blood cells, now substantially free of white blood cells, are then conveyed from the transfer container back to the primary collection container for storage through the second fluid path, this time bypassing the separation device.

A need still exists for further improved systems and methods for removing undesired matter from blood components prior to transfusion or storage in a way that lends itself to use in closed multiple blood bag system environments.

SUMMARY OF THE INVENTION

The invention provides a multiple container blood collection system for conveniently processing all the various components of blood. The system includes a device for separating undesired matter from some of the components prior to storage. The system is arranged so that only a single pass through the separation device is required during a given processing sequence.

In one embodiment, the system comprises a blood collection assembly and an associated transfer assembly having first and second transfer containers.

Two transfer paths lead to the first transfer container. The first transfer path includes means for separating undesired matter from blood. A second transfer path bypasses the separation means.

A third transfer path leads to the second transfer container. The third path communicates with the second transfer path, also bypassing the separation means that is present in the first transfer path.

The system also includes means for establishing communication between the blood collection assembly and the first, second and third transfer paths.

In this arrangement, the system includes flow control means that is operable in three modes:

(i) In its first mode, the flow control means directs a first quantity of blood from the blood collection assembly for collection in the second transfer container through the second and third transfer paths, therefore bypassing the separation means. In this way, a first quantity of blood can be freely and easily transferred within the system without being passed through the separation means.

(ii) In its second mode, the flow control means directs a second quantity of blood from the blood collection assembly to the first transfer container through the first transfer path. In this way, the second quantity of blood can be passed through the separation means for removal of the undesirable matter.

(iii) In its third mode, the flow control means directs the second quantity of blood (now substantially free of undesired matter) from the first transfer container back to the blood collection assembly for storage. This transfer occurs through the second flow path, thereby bypassing the separation means. In this way, blood previously freed of undesired matter can be easily transferred back to the blood collection system for storage without being unnecessarily subjected to a second pass through the separation means.

In a preferred arrangement, the blood collection assembly includes a satellite bag which contains an additive solution for the blood that is to be stored free of undesired matter. In this arrangement, the flow control means is operative in a fourth mode for directing the additive solution from the satellite bag to the primary container through a path that bypasses the separation means. The additive solution is added to a blood component prior to its being passed through the separation device. As in the other arrangements, the system facilitates multiple blood component processing with only a single pass through the inline separation means.

In a preferred embodiment, the blood collection assembly and the transfer assembly comprise separate closed subassemblies. In this arrangement, the means for establishing communication includes means for attaching the blood collection subassembly to the transfer subassembly without otherwise opening the closed subassemblies to communication with the atmosphere.

The invention also provides methods of collecting blood components substantially free of undesired matter using the systems as just generally described.

Other features and advantages of the invention will become apparent upon review of the following description, drawings, and appended claims.

BRIEF DESCRIPTION OF THE DRAWINGS

FIG. 2 is a schematic view of the system shown in FIG. 1, with the blood transfer assembly attached to the blood processing assembly showing transfer of plasma and platelet components to a transfer container;

FIG. 3 is a schematic view of the system shown in FIG. 1, showing filtration of the red blood cells to remove undesired matter, with the platelet and plasma being independently processed in a separate subassembly;

DESCRIPTION OF THE PREFERRED EMBODIMENTS

Figure 1:
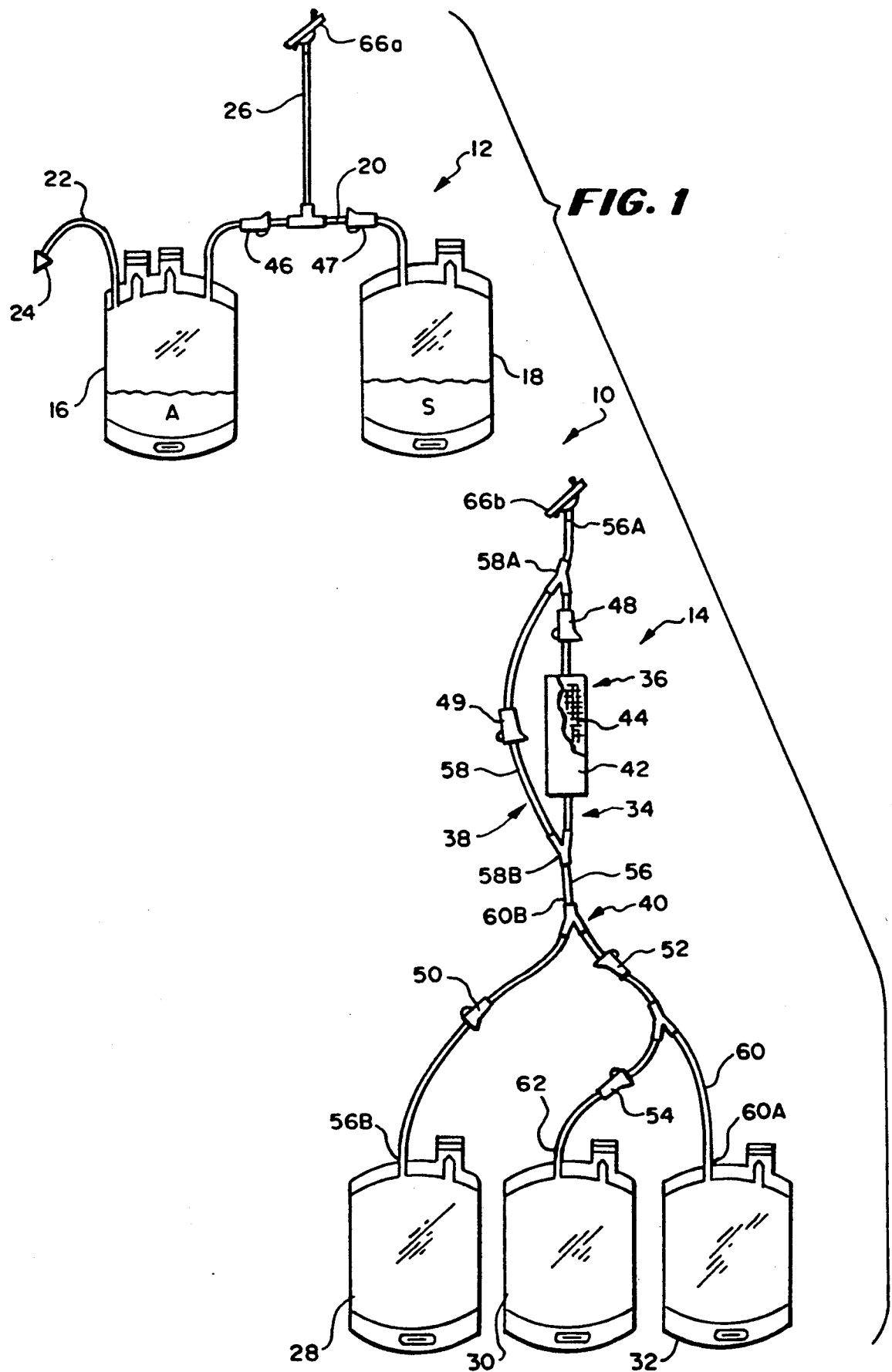
FIG. 1 is a schematic view of a blood collection system that includes a blood processing assembly and a transfer assembly that embody the features of the invention.

A blood collection system 10 that embodies the features of the invention is shown in FIG. 1. The system 10 comprises a blood collection assembly 12 and a transfer assembly 14.

In use, the assembly 12 serves to initially collect a unit of blood from a donor and to allow conventional centrifugal separation of the blood into at least two component parts. The assembly 12 serves to process the blood into first and second component parts. In use, the assembly 14 also serves to allow the separation of undesired matter from the second component prior to the storage.

In the embodiment shown in FIG. 1, the transfer assembly 14 comprises an initially separate subassembly that is not joined to the blood processing assembly 12. In this arrangement, the assembly 12 also becomes an initially separate subassembly.

According to the invention, prior to use, the separate transfer subassembly 14 need not contain any fluids, storage mediums, and the like (except for any entrapped air). Preferably, all such fluids are contained in the blood collection subassembly 12 prior to use. The invention thus provides the capability of having a blood collection system 10 composed of a fluid containing (or "wet") subassembly 12 and a fluid free (or "dry") subassembly 14. This arrangement serves to avoid the application of the regulatory requirements governing fluid-containing systems upon the transfer assembly 14. It should be appreciated, however, that the transfer assembly 14 can be made as an integral part of the assembly 12 and/or, if desired, contain fluids.

In the embodiment shown in FIG. 1, the blood collection and storage subassembly 12 comprises a blood bag system having a primary bag or container 16 and a satellite bag or container 18 attached to the primary bag 16 by integrally attached tubing 20.

In use, the primary bag 16 (which is also called a donor bag) receives whole blood from a donor through integrally attached donor tubing 22 that carries an phlebotomy needle 24. A suitable anticoagulant A is contained in the primary bag 16.

The whole blood is separated by conventional centrifugation techniques within the primary bag 16 into a red blood cell component and a platelet-rich plasma component. During such separation techniques, a layer of white blood cells (commonly called the "buffy coat") forms between the red blood cells and the platelet-rich plasma.

The tubing 20 that integrally connects the bags 16 and 18 is also joined to an outlet branch tubing 26 for connection to the transfer subassembly 14.

The transfer assembly 14 includes several transfer bags or containers 28, 30, and 32. The transfer bag 28 is intended to receive red blood cells in the course of removing white blood cells from the red blood cells prior to storage. The transfer containers 30 and 32 are intended to accommodate the separation of the platelets from the platelet-rich plasma and to ultimately store the resulting platelet-poor plasma and concentrated platelet components.

In the illustrated embodiment, the transfer bag 32 ultimately serves as the storage container for the platelet concentrate, and the transfer bag 30 ultimately serves as the storage container for the platelet-poor plasma.

The transfer assembly 14 includes a first transfer path 34 that leads to the transfer container 28. The path 34 includes a device 36 for separating undesired matter cells from blood.

It should be appreciated that the transfer assembly 14 can be used to remove all types of undesired materials from different types blood cells, depending upon its particular construction. In the illustrated embodiment, the assembly 14 is intended to remove white blood cells (and preferably also platelets) from the red blood cells prior to storage. In this arrangement, the separation device 36 includes a housing 42 containing a conventional filtration medium 44 suited for the removal of white blood cells and platelets from red blood cells. The filtration medium 44 can include cotton wool, cellulose acetate or another synthetic fiber like polyester.

It should also be appreciated that separation can occur by various centrifugal and non-centrifugal techniques, and not merely "filtration" in the technical sense. Separation can occur by absorption, columns, chemical, electrical, and electromagnetic means. The term "separation device" is broadly used in this specification encompass all of these separation techniques as well.

The transfer assembly 14 further includes a second transfer path 38 that also leads to the transfer container 28. However, unlike the transfer path 34, this transfer path 38 bypasses the separation device 36.

The transfer assembly 14 also includes a third transfer path 40 that communicates with the second transfer path 38. The third path 40 leads to the transfer container 32, bypassing the separation device 36.

Because of this construction, it is possible to selectively direct fluid within the system 10 into and out of the containers 28, 30, and 32 in paths that either pass through the separation device 36 (i.e., via the fluid path 34) or bypass the separation device 36 (i.e., via the fluid path 38).

The assembly 14 can be variously constructed. In the illustrated embodiment, fluid path 34 takes the form of a length of flexible tubing 56. The tubing 56 includes first and second opposite end portions 56A and 56B. The tubing end 56B is connected to the transfer container 28. The separation device 36 is located inline between the opposite end portions 56A and 56B.

In this arrangement, the fluid path 38 also includes a length of flexible tubing 58. One end 58A joins the first fluid path tubing 56 between tubing end 56A and the separation device 36. The other end 58B joins the first fluid path tubing 56 between the separation device 36 and the tubing end 56B.

In this arrangement, the fluid path 40 also includes a length of flexible tubing 60. One end 60A is connected to the transfer container 32. The other end 60B joins the tubing 56 between its junction with tubing end 58B and its tubing end 56B. A length of flexible tubing 62 attached to the transfer container 30 joins the tubing 60 between tubing ends 60A and 60B.

The transfer assembly 14 includes flow control means for directing fluid flow between the collection subassembly 12 and the various paths 34, 28, and 40 of the transfer subassembly 14. In the illustrated embodiment, the flow control means comprise a series of conventional roller clamps 46 to 54 arranged as shown in FIG. 1. By selectively opening and closing the roller clamps 46 to 54, the system 10 can be selectively placed by the user in different processing modes.

A first processing mode directs a first quantity of blood from the assembly 12 for collection in the transfer container 32 via the second and third transfer paths 38 and 40. The first quantity of collected blood thereby bypasses the separation device 36.

A second processing mode directs a second quantity of blood from the assembly 12 to the transfer container 28 via the first transfer path 34. The second quantity of blood thereby passes through the separation device 36 to remove the undesired materials. This mode is intended to be used to remove undesired matter from those components prior to storage.

A third mode directs the second quantity of blood from the transfer container 28 back to the assembly 12 via the second flow path 38 for storage, thereby bypassing the separation device 36. This mode avoids the unnecessary return of filtered components back through the separation device 36.

The bags and transfer paths associated with the assemblies 12 and 14 can be made from conventional approved medical grade plastic materials, such as polyvinyl chloride plasticized with di-2-ethylhexylphthalate (DEHP). Alternatively, transfer container 32, which is intended to store the platelet concentrate, can be made of polyolefin material (as disclosed in Gajewski et al U.S. Pat. No. 4,140,162) or a polyvinyl chloride material plasticized with tri-2-ethylhexyl trimellitate (TEHTH). These materials, when compared to DEHP-plasticized polyvinyl chloride materials, have greater gas permeability that is beneficial for platelet storage.

The system 10 includes a means for connecting the initially separate subassemblies 12 and 14 together for use. The connection means is associated with each of the initially separate assemblies 12 and 14. The connection means permits selective attachment of the transfer assembly 14 to the blood collection assembly 12 (as shown in FIG. 2).

In the embodiment shown in FIG. 1, the connection means comprises two mating sterile connection devices (designated 66a and 66b). The devices 66a and 66b (see also FIG. 7) are described in Granzow et al U.S. Pat. Nos. 4,157,723 and 4,265,280, which are incorporated herein by reference. One device 66a is carried by the outlet branch 26 of the assembly 12. The other device 66b is carried at the tubing end 56A of the transfer assembly 14.

Figure 7:
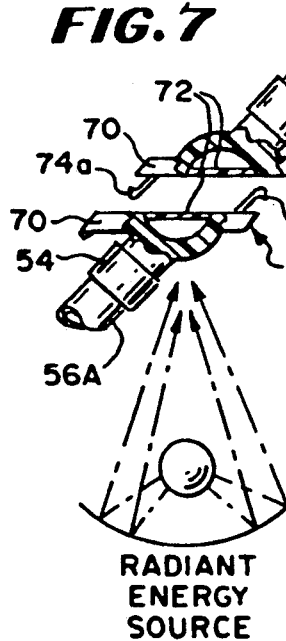
FIG. 7 is an enlarged side sectional view of the sterile connection devices associated with the shown in FIGS. 1 and 6.

As shown in FIG. 7, the sterile connection devices 66a and 66b each generally includes a housing 70 having a normally closed, meltable wall 72 made of a radiant energy absorbing material. The housings 70 are joined together with mating bayonet-type couplers 74a and 74b, with the walls 72 placed in facing contact. When connected and exposed to radiant energy, the walls 72 melt at temperatures that result in the destruction of bacteria, while at the same time opening a fluid path between the connected housings 70.

The devices 66a and 66b normally close the associated assemblies 12 and 14 from communication with the atmosphere and are opened in conjunction with an active sterilization step which serves to sterilize the regions adjacent to the interconnecting fluid path as the fluid path is being formed. These devices 66a and 66b also hermetically seal the interconnecting fluid path at the time it is formed. The use of these sterile connection devices 66a and 66b is a probability of non-sterility that exceeds one in a million. The devices 66a and 66b thus serve to connect the two assemblies 12 and 14 without compromising the sterile integrity of either.

Alternately, the connection means can comprise the sterile connecting system disclosed in Spencer U.S. Pat. No. 4,412,835 (not shown). In this arrangement, this system forms a molten seal between the tubing end 26 and 56A. Once cooled, a sterile weld is formed.

The assemblies 12 and 14, once sterilized, each constitutes a sterile, "closed" system, as judged by the applicable standards in the United States.

In use, whole blood is collected (via the donor tube 22) in the primary bag 16. The collected whole blood is then separated within the primary bag 16, preferably by centrifuging, into red blood cells (RBC) and platelet-rich plasma (PRP). An intermediate white blood cell layer (BC) also forms.

The assembly 12 is next joined to the assembly 14 (as FIG. 2 shows). The flow control means is placed into its first processing mode by closing clamps 47; 48; 50; and 54 (if previously opened) and by opening clamps 46; 49; and 52 (if previously closed).

The platelet-rich plasma (PRP) is conveyed from the primary bag 16 through second and third transfer paths 38 and 40 by conventional techniques (for example by using a plasma expresser) into the transfer bag 32. In this step, attempts are made to leave all the red blood cells and as many white blood cells as possible in the primary bag 16. The handling of the platelet-rich components in this way avoids use of the separation device 36.

The clamp 52 is closed, and the transfer bags 30 and 32 are detached in a sterile fashion (as FIG. 3 shows). The detachment can be accomplished using a conventional heat sealing device (for example, the Hematron® dielectric sealer sold by Baxter Healthcare Corporation), which forms a hermetic, snap apart seal in the tubing 60 (this seal is schematically shown by an "x" in FIG. 3 ). The donor tubing 22 is preferably sealed and disconnected in the same fashion (as shown in FIG. 2) before joining the two assemblies 12 and 14 together.

As FIG. 3 also shows, the platelet-rich plasma can undergo subsequent centrifugal separation within the transfer bag 32 into platelet concentrate (designated PC in FIG. 3) and platelet-poor plasma (designated PPP in FIG. 3). By opening clamp 54, the platelet-poor plasma (PPP) is transferred into the bag 30 for storage, leaving the platelet concentrate in the bag 32. The transfer bags 30 and 32 are then separated by the snap-apart seals "x" in the tubing 32 (as shown in FIG. 3) for subsequent storage as individual components.

The flow control means is next placed into its second processing mode to transfer the red blood cells (with associated white blood cells) to the transfer container 28 via the separation device 36.

In the illustrated embodiment, the satellite container 18 holds a suitable storage solution S for red blood cells. One such solution is disclosed in Grode et al U.S. Pat. No. 4,267,269. In this arrangement, prior to assuming the second processing mode, the flow control means is first placed into a processing mode for directing the additive solution S from the satellite bag 18 to the primary bag in a path that bypasses the separation device 36. This mode is accomplished by closing clamp 48 and opening clamps 46 and 47. The solution A is transferred to the primary bag 16 via path 20.

The second processing mode then proceeds by closing clamps 47 and 49 and opening clamp 48. As shown in FIG. 3, the primary bag 16 is lifted above the transfer bag 28, and the red blood cells (with associated white blood cells and additive solution S) are conveyed by gravity flow from the bag 16 through the fluid path 34 and separation device 36 into the transfer bag 28. The undesired matter (i.e., white blood cells and platelets) are removed from the red blood cells by the separation device 36.

Figure 4:
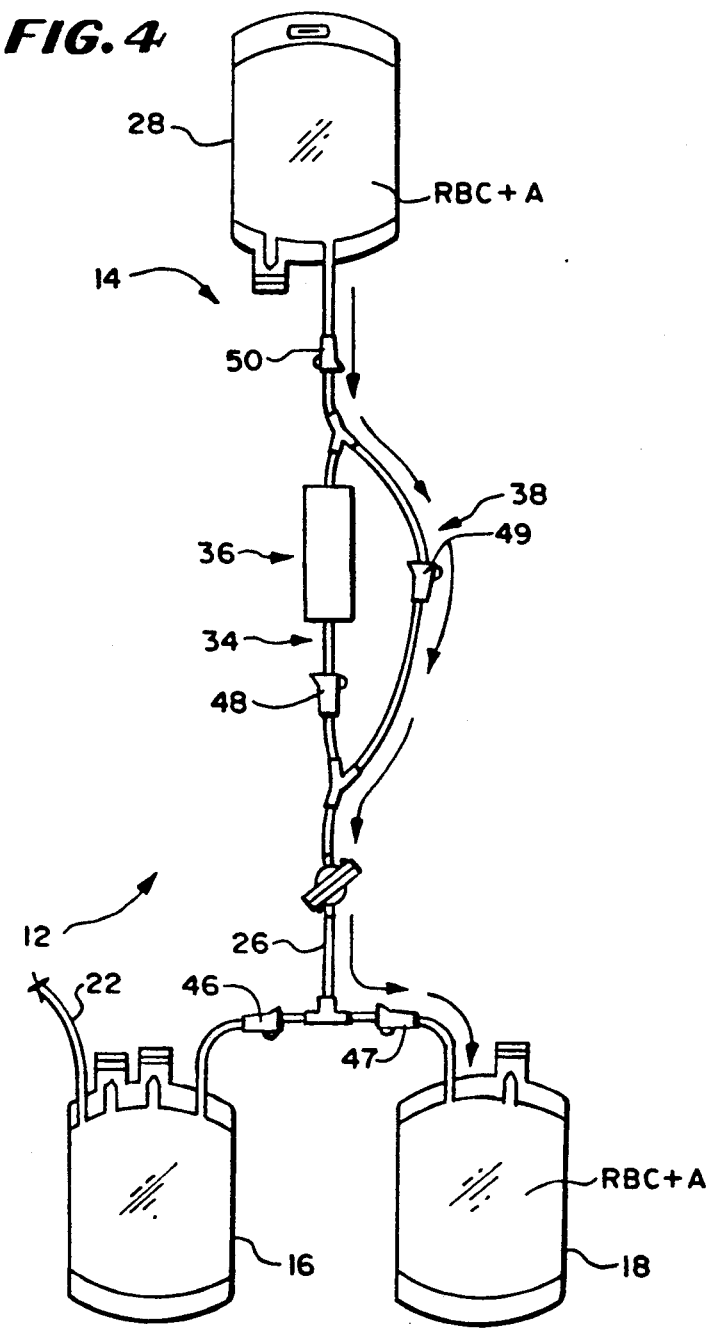
FIG. 4 is a schematic view of the system shown in FIG. 1, showing the return of the filtered blood cells to the collection assembly for storage.

While the two assemblies 12 and 14 are still attached together, the flow control means is placed in its third mode, as FIG. 4 shows. This is accomplished by closing clamp 48 and opening clamp 49. The transfer bag 28 is lifted above assembly 12. The red blood cells and additive solution, now substantially free of the undesired white blood cells, are returned by gravity flow from the transfer bag 28 through the fluid path 38, bypassing the separation device 36.

The filtered red blood cells can be returned for storage either to the primary bag 16 (by opening clamp 46 and closing clamp 47) or to the now empty satellite bag 18 (by closing clamp 46 and opening clamp 47). In the illustrated and preferred embodiment, the filtered red blood cells are conveyed to the satellite bag 18 for storage.

Should air be trapped in the transfer bag 28, it may be necessary to first transfer the air through bypass path 38 into the bag 16 or 18 in which the red blood cells will not be ultimately returned for storage.

Figure 5:
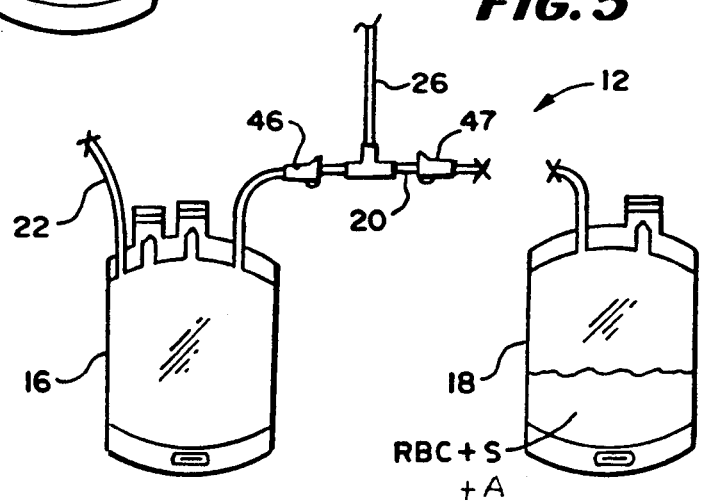
FIG. 5 is a schematic view of the system shown in FIG. 1 with the container holding the filtered blood separated from the system for storage.

As FIG. 5 shows, the satellite bag containing the filtered red blood cells and additive solution is detached from the blood collection assembly 12 for storage.

In one alternative arrangement (not shown), the assembly 12 could be made without an associated satellite bag 18. In this arrangement, the red blood cells are returned to the primary bag 16 for storage after filtration.

In another alternative arrangement (also not shown), the assembly 12 could include an associated empty satellite bag, without an additive solution. In this arrangement, the red blood cells are returned to the satellite bag after filtration for storage free of an additive solution.

Figure 6:
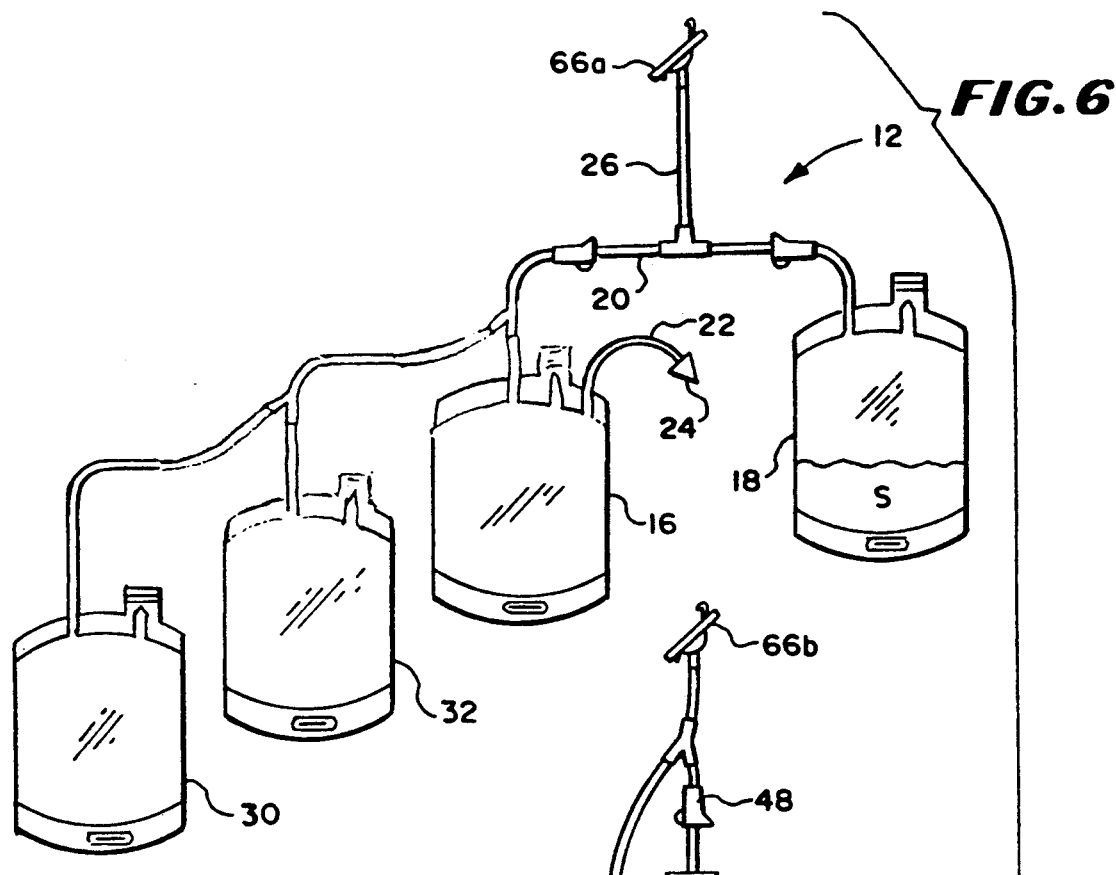
FIG. 6 is a schematic view of another blood collection system that includes a blood processing assembly and a transfer assembly that embody the features of the invention.

Yet another alternative arrangement is shown in FIG. 6. In this embodiment, like the embodiment shown in FIG. 1, the assembly 12 includes a primary bag 16 and a satellite bag 18. Also like the embodiment shown in FIG. 1, the assembly 14 includes a transfer container 28 with two associated flow paths 34 and 38, one 34 which includes the separation device 36, one 38 which does not.

Unlike the FIG. 1 embodiment, the transfer bags 30 and 32 are not associated with the assembly 14, but instead form an integral part of the assembly 12.

In using the embodiment shown in FIG. 6, whole blood is collected in the donor bag 16, where it is separated into red blood cells, platelet-rich plasma, and white blood cells in the manner already described in the FIG. 1 embodiment. In its first processing mode, the platelet-rich plasma is conveyed to the transfer bag 32 for processing. Like the FIG. 1 embodiment, the path between the primary bag 16 and the transfer bags 30 and 32 bypasses the separation device 36.

The transfer bags 30 and 32 are then detached from the assembly 12 in the manner previously described with respect to assembly 14. The assembly 12 is then attached to the assembly 14, and the processing through the remaining modes proceeds as previously described.

In the illustrated embodiments, the entire filtration process (including the attachment and detachment of the assemblies 12 and 14) can be accomplished in less than five minutes. All blood components processed are substantially free of the undesired matter. In the preferred embodiment, where the all the fluid transfers are made using sterile connection techniques, the processing and inline filtration have occurred without compromising the sterile integrity of any collected component or reducing their storage life.

Various modifications of the invention will be apparent to those skilled in the art within the purview of the following claims.

We claim:

1. A method of collecting blood components comprising the steps of
    collecting blood having the undesired matter in a blood collection assembly,
    separating the blood in the blood collection assembly into a first component and a second component that contains undesired matter,
    opening communication between the blood collection assembly and first and second transfer assemblies,
    the first transfer assembly having a first transfer container, a first transfer path that leads to the first transfer container and that includes means for separating the undesired matter from the blood, a second transfer path that leads to the first transfer container and that bypasses the separation means, and
    the second transfer assembly having a second transfer container and a third transfer path that communicates with the second transfer path and that leads to the second transfer container bypassing the separation means,
    conveying the first component to the second transfer container through the second and third transfer paths, thereby bypassing the separation means,
    conveying the second component to the first transfer container through the first transfer path, thereby passing the second component through the separation means to remove the undesired matter, and
    transferring the second component, now substantially free of the undesired matter, from the first transfer container back through the second transfer path to the blood collection assembly for storage.

2. A method according to claim 1
    wherein the step of opening communication between the blood collection assembly and the first and second transfer assemblies includes joining the first and second transfer assemblies to the blood collection assembly.

3. A method according to claim 1
    and further including the step, which occurs after the step of conveying the first component to the second transfer container, of separating the second transfer assembly from the blood collection assembly.

4. A method according to claim 1
    and further including the step, which occurs after the step of conveying the second component back to the blood collection assembly, of separating the first transfer assembly from the blood collection assembly.

5. A method according to claim 1 or 3
    and further including the step, which occurs after the step of conveying the first component to the second transfer container, of separating the first component into additional component parts within the second transfer assembly.

6. A method of collecting blood components comprising the steps of
    collecting blood having the undesired matter in a blood collection assembly that has a collection container, in which the blood is collected, and a satellite container,
    separating the blood in the collection container into a first component and a second component that contains undesired matter,
    opening communication between the first container of the blood collection assembly and first and second transfer assemblies,
    the first transfer assembly having a first transfer container, a first transfer path that leads to the first transfer container and includes means for separating the undesired matter from the blood, and a second transfer path that leads to the first transfer container and that bypasses the separation means, and
    the second transfer assembly having a second transfer container and a third transfer path that communicates with the second transfer path and that leads to the second transfer container bypassing the separation means,
    conveying the first component from the collection container to the second transfer container through the second and third transfer paths, thereby bypassing the separation means,
    conveying the second component from the collection container to the first transfer container through the first transfer path, thereby passing the second component through the separation means to remove the undesired matter, and
    opening communication between the satellite container and the second transfer path to transfer the second component, now substantially free of the undesired matter, from the first transfer container through the second transfer path into the satellite container for storage.

7. A method according to claim 6
    wherein the satellite container holds an additive solution for the second component,
    and further including the step, which occurs prior to the step of conveying the second component to the first transfer container through the separation means, of transferring the additive solution to the first container.

8. A method according to claim 7
    wherein the step of opening communication between the first container and the first and second transfer assemblies includes joining the first and second transfer assemblies to the blood collection assembly.

9. A method according to claim 7
    and further including the step, which occurs after the step of conveying the first component to the second transfer container, of separating the second transfer assembly from the blood collection assembly.

10. A method according to claim 7
and further including the step, occurring after the step of conveying the second component to the satellite container, of separating the satellite container from the blood collection assembly.

11. A method according to claim 7 or 8
and further including the step, occurring after the step of conveying the first component to the second transfer container, of separating the first component into additional component parts within the second transfer assembly.

12. A method of collecting blood components comprising the steps of
collecting blood having the undesired matter in a blood collection assembly that has a collection container, in which the blood is collected, and a satellite container,
separating the blood in the collection container into a first component and a second component that contains the undesired matter,
opening communication between the blood collection assembly and first and second transfer assemblies,
the first transfer assembly having a first transfer container, a first transfer path that leads to the first transfer container and includes means for separating the undesired matter from the blood, and a second transfer path that leads to the first transfer container bypassing the separation means, and
the second transfer assembly having a second transfer container and a third transfer path that leads to the second transfer container and that bypasses the separation means,
conveying the first component from the collection container to the second transfer container through the third transfer path, thereby bypassing the separation means,
conveying the second component from the collection container to the first transfer container through the first transfer path, thereby passing the second component through the separation means to remove the undesired matter, and
transferring the second component, now substantially free of the undesired matter, from the first transfer container back through the second transfer path to the satellite container of blood collection assembly for storage.

13. A method according to claim 12
wherein the satellite container holds an additive solution for the second component,
and further including the step, which occurs prior to the step of conveying the second component to the first transfer container through the separation means, of transferring the additive solution from the satellite container to the collection container.

14. A method according to claim 12
wherein the step of opening communication between the blood collection assembly and the first and second transfer assemblies includes joining the first and second transfer assemblies to the blood collection assembly.

15. A method according to claim 12
and further including the step, which occurs after the step of conveying the first component to the second transfer container, of separating the second transfer assembly from the blood collection assembly.

16. A method according to claim 12
and further including the step, which occurs after the step of conveying the second component to the satellite container, of separating the satellite container from the blood collection assembly.

17. A method according to claim 12 or 14
and further including the step, which occurs after the step of conveying the first component to the second transfer container, of separating the first component into additional component parts within the second transfer assembly.

18. A method of collecting blood components comprising the steps of:
collecting in a first container a first blood component that comprises plasma and platelets and a second, red blood cell-containing component that includes white blood cells,
opening communication between the first container and a transfer assembly to convey the first blood component from the first container into a transfer assembly,
separating the transfer assembly containing the first blood component from the first container,
opening communication between the first container and a satellite container that contains an additive solution to convey the additive solution into the first container,
opening communication between the first container and another transfer assembly through a fluid path that includes means for separating white blood cells from blood to convey the second, red blood cell-containing component, now with additive solution, to the other transfer assembly while at the same time separating the white blood cells from the red blood cells,
opening communication between the other transfer assembly and the satellite container through a fluid path that bypasses the separation means to convey the red blood cells, now with additive solution but substantially free of white blood cells, from the other transfer assembly into the satellite container through the fluid path that bypasses the separation means, and
separating the satellite container containing the red blood cells substantially free of white blood cells for storage.

19. A method according to claim 18
and further including the step, which occurs after the step of separating the transfer assembly containing the first component, of separating the first component into a plasma component and a platelet component within the separated transfer assembly.

20. A blood collection system comprising
a blood collection assembly including an outlet flow path,
a transfer assembly including
a first transfer container,
a second transfer container,
a first transfer path that leads to the first transfer container and that includes means for separating the undesired matter from blood,
a second transfer path that leads to the first transfer container and that bypasses the separation means, and
a third transfer path that communicates with the second transfer path and that leads to the second transfer container bypassing the separation means, means for directing fluid flow between the outlet flow path and the first, second and third transfer paths including flow control means operable (i) in a first mode for directing a first quantity of blood from the blood collection assembly for collection in the second transfer container through the second and third transfer paths, the first quantity of collected blood thereby bypassing the separation means;

(ii) in a second mode for directing a second quantity of blood from the blood collection assembly to the first transfer container through the first transfer path, the second quantity of the blood thereby passing through the separation means to remove the undesired materials; and (iii) in a third mode for directing the second quantity of blood from the first transfer container back to the blood collection assembly through the second flow path for storage, thereby bypassing the separation means.

21. A blood collection system according to claim 20 wherein the blood collection assembly includes a primary container and a satellite container, wherein the outlet flow path includes a first branch that communicates with the primary container and a second branch that communicates with the satellite container, and wherein, when operated in its first and second modes, the flow control means directs the first and second quantities of blood from the primary container, and when operated in its third mode, the flow control means directs the second quantity of blood from the first transfer container to the satellite container and not the primary container.

22. A blood collection system according to claim 21 wherein the satellite container contains an additive solution, and wherein the flow control means is operative in a fourth mode for directing the additive solution from the satellite container to the primary container through the first and second branches, bypassing the separation means.

23. A blood collection system according to claim 20 wherein the blood collection assembly and the transfer assembly comprise separate subassemblies, and wherein the means for establishing communication includes means for attaching the blood collection subassembly to the transfer subassembly.

24. A blood collection system according to claim 20 wherein the blood collection subassembly includes a primary container and a satellite container, wherein the outlet flow path includes a first branch that communicates with the primary container and a second branch that communicates with the satellite container, and wherein, when operated in its first and second modes, the flow control means directs the first and second quantities of blood from the primary container, and when operated in its third mode, the flow control means directs the second quantity of blood from the first transfer container to the satellite container and not the primary container.

25. A blood collection system according to claim 24 wherein the satellite container contains an additive solution, and wherein the flow control means is operative in a fourth mode for directing the additive solution from the satellite container to the primary container through the first and second branches, bypassing the separation means.

26. A blood collection system according to claim 20 wherein the blood collection assembly and the transfer assembly each comprise a separate closed subassembly, and wherein the means for establishing communication includes connection means associated with the transfer subassembly and the blood collection subassembly for attaching and detaching the collection and transfer subassemblies in a manner that preserves the sterile integrity of the closed subassemblies.

27. A blood collection system comprising a blood collection assembly including a primary container having a first and second outlet branches, a satellite container that communicates with the first outlet branch of the primary container, a first transfer assembly including
a transfer container,
a first transfer path that leads to the first transfer container and that includes means for separating the undesired matter from blood, and
a second transfer path that leads to the first transfer container and that bypasses the separation means, a second transfer assembly including a third transfer path that bypasses the separation means, means for establishing communication between the first outlet branch of the primary container and the first and second transfer paths, means for establishing communication between the second outlet branch of the primary container and the third transfer path, and flow control means operable (i) in a first mode for directing a first quantity of blood from the primary container for collection in the second transfer assembly through the third transfer path, the first quantity of collected blood thereby bypassing the separation means;

(ii) in a second mode for directing a second quantity of blood from the primary container to the first transfer container through the first transfer path, the second quantity of the blood thereby passing through the separation means to remove the undesired materials; and (iii) in a third mode for directing the second quantity of blood from the first transfer container back to the satellite container through the second flow path for storage, thereby bypassing the separation means.

28. A blood collection system according to claim 27 wherein the satellite container contains an additive solution, and wherein the flow control means is operative in a fourth mode for directing the additive solution from the satellite container to the primary container through the second outlet branch, bypassing the separation means.

29. A blood collection system according to claim 27 wherein the blood collection assembly and the first transfer assembly comprise separate subassemblies, and wherein the means for establishing communication includes means for attaching the first outlet branch of the primary container to the first transfer subassembly.

30. A blood collection system according to claim 27 or 29 wherein the second transfer assembly is integrally connected to the second outlet branch of the primary container.

31. A blood collection system according to claim 27 wherein the blood collection assembly and at least the first transfer assembly each comprise a separate closed subassembly, and
wherein the means for establishing communication includes connection means associated with the first transfer subassembly and the blood collection subassembly for attaching and detaching the collection and first transfer subassemblies in a manner that preserves the sterile integrity of the closed subassemblies.

32. An assembly usable in association with a primary blood collection system comprising a primary container, for removing undesired matter from blood cells, the separation assembly comprising a temporary transfer container and an interconnected transfer/storage container,
a first fluid path communicating with the temporary transfer container and having an inline separation means for separating undesired matter from blood cells,
a second fluid path individually communicating with each transfer container and bypassing the separation means,
flow control means associated with the first and second flow paths operable in a first mode for directing fluid through the second flow path into the transfer/storage container, bypassing the separation means; in a second mode for directing fluid through the first flow path into the temporary transfer container through the separation means to remove undesired matter therefrom; and in a third mode for directing fluid from the temporary transfer container through the second flow path bypassing the separation means, and
means for establishing communication between the separation assembly and the collection assembly.

* * * * *